(12) United States Patent
Kirveskari et al.

(10) Patent No.: US 9,868,995 B2
(45) Date of Patent: Jan. 16, 2018

(54) **METHOD FOR DETECTING *HELICOBACTER PYLORI* DNA IN A STOOL SAMPLE**

(71) Applicant: AMPLIDIAG OY, Helsinki (FI)

(72) Inventors: Juha Kirveskari, Espoo (FI); Hilpi Rautelin, Helsinki (FI)

(73) Assignee: AMPLIDIAG OY, Helsinki (FI)

( * ) Notice: Subject to any disclaimer, the term of this patent is extended or adjusted under 35 U.S.C. 154(b) by 217 days.

(21) Appl. No.: 14/649,674

(22) PCT Filed: Dec. 5, 2013

(86) PCT No.: PCT/FI2013/051144
§ 371 (c)(1),
(2) Date: Jun. 4, 2015

(87) PCT Pub. No.: WO2014/087055
PCT Pub. Date: Jun. 12, 2014

(65) Prior Publication Data
US 2016/0017406 A1    Jan. 21, 2016

(30) Foreign Application Priority Data
Dec. 5, 2012   (FI) ..................................... 20126271

(51) Int. Cl.
*C12P 19/34*   (2006.01)
*C12Q 1/68*    (2006.01)

(52) U.S. Cl.
CPC ....... *C12Q 1/689* (2013.01); *C12Q 2600/156* (2013.01)

(58) Field of Classification Search
CPC .............. C12C 1/689; C12C 2600/156; C12C 2600/1564
USPC ...................................................... 435/91.2
See application file for complete search history.

(56) References Cited

FOREIGN PATENT DOCUMENTS

| JP | 2005-168474 A | 6/2005 |
|---|---|---|
| JP | 2006-20511 A | 1/2006 |
| JP | 101665824 A | 3/2010 |
| JP | 2010-233505 A | 10/2010 |
| JP | 2011-62143 A | 3/2011 |
| WO | WO 2007/106407 A2 | 9/2007 |

OTHER PUBLICATIONS

Booka et al. "Polymerase Chain Reaction-Restriction Fragment Length Polymorphism Analysis of Clarithromycin-Resistant Helicobacter pylori Infection in Children Using Stool Sample", Helicobacter, Jun. 2005, vol. 10, No. 3, pp. 205-213.
Fontana et al. "Detection of Clarithromycin-Resistant Helicobacter pylori in Stool Samples", Journal of Clinical Microbiology, Aug. 2003, vol. 41, No. 8, pp. 3636-3640.
International Search Report, issued in PCT/FI2013/051144, dated Feb. 4, 2014.
Noguchi et al. "Detection of mixed clarithromycin-resistant and -susceptible Helicobacter pylori using nested PCR and direct sequencing of DNA extracted from faeces", Journal of Medical Microbiology, (2007), 56, 1174-1180.
Rimbara et al. "Development of a Highly Sensitive Method for Detection of Clarithromycin-Resistant Helicobacter pylori from Human Feces", Current Microbiology, vol. 51, (2005), pp. 1-5.
Schabereiter-Gurtner et al. "Novel Real-Time PCR Assay for Detection of Helicobacter pylori Infection and Simultaneous Clarithromycin Susceptibility Testing of Stool and Biopsy Specimens", Journal of Clinical Microbiology, vol. 42, No. 10, Oct. 1, 2004, pp. 4512-4518.
Search Report issued in Finland priority application No. 20126271, dated Aug. 28, 2013.
Written Opinion of the International Searching Authority, issued in PCT/FI2013/051144, dated Feb. 4, 2014.
Xing et al. "Development of a Microelectronic Chip Array for High-Throughput Genotyping of Helicobacter Species and Screening for Antimicrobial Resistance", Journal of Biomolecular Screening, vol. 10, No. 3, Apr. 1, 2005, pp. 235-245.

*Primary Examiner* — Cynthia B Wilder
(74) *Attorney, Agent, or Firm* — Birch, Stewart, Kolasch & Birch, LLP

(57) ABSTRACT

The present invention provides a PCR based method for detecting chronic gastritis causing bacterium, namely *Helicobacter pylori*, in a stool sample. The present invention is based on the use of oligonucleotide primers and probes specific to *H. pylori* 23S rRNA gene.

5 Claims, 3 Drawing Sheets

METHOD FOR DETECTING *HELICOBACTER PYLORI* DNA IN A STOOL SAMPLE

REFERENCE TO SEQUENCE LISTING SUBMITTED VIA EFS-WEB

This application includes an electronically submitted sequence listing in .txt format. The .txt file contains a sequence listing entitled "2015-09-17_0933-0661PUS1_ST25.txt" created on Sep. 17, 2015 and is 7,436 bytes in size. The sequence listing contained in this .txt file is part of the specification and is hereby incorporated by reference herein in its entirety.

The present invention relates to the field of polymerase chain reaction (PCR) based diagnostic assays. More specifically, the present invention provides a PCR based method for detecting chronic gastritis causing bacteria, namely *Helicobacter pylori*, in a stool sample. The present invention is based on the use of oligonucleotide primers and probes specific to the *H. pylori* 23S rRNA gene.

BACKGROUND OF THE INVENTION

*H. pylori* is a gram-negative and microaerophilic bacterium, which causes chronic gastritis. It is estimated that about half of the world's population are infected with this bacterium. Most of the *H. pylori* infected individuals are asymptomatic despite gastritis but a minority will develop severe sequelae. *H. pylori* is the key factor in the development of duodenal or gastric ulcers, and the most common single risk factor for non-cardia gastric cancer. The successful eradication of *H. pylori* infection leads to healing of peptic ulcer disease (Ford et al, 2003) and in long-term relief of dyspeptic symptoms even in some patients without ulcers (Ford et al., 2004). Eradication therapy of *H. pylori* infection is also recommended as the first-line treatment for low-grade mucosa-associated lymphoid tissue (MALT) lymphoma and on the basis of epidemiological studies successful *H. pylori* eradication therapy may lead to a decreased number of gastric cancer cases (Kosunen et al, 2011; Chey and Wong, 2007).

Diagnostic methods for the detection of *H. pylori* infection can be divided into invasive (gastroscopy is required) and non-invasive methods. Although several methods give highly accurate results, there is not a single gold standard for the diagnosis of *H. pylori* infection but the selection of the methods depends on the clinical situation and if there is otherwise a need for gastroscopy. According to the test-and treat strategy, patients with a low risk for gastric cancer can be tested for *H. pylori* with non-invasive methods and treated if *H. pylori* is detected.

Although non-invasive diagnostic methods, such as urea breath tests and stool antigen tests, in general show highly accurate detection rates, these methods do not give any information on the antimicrobial susceptibility of the infecting isolate of *H. pylori*. Furthermore, even if gastric biopsies are taken in gastroscopy and sent for culture, antimicrobial susceptibility testing results are usually not available in all positive cases due to the low sensitivity of culture. However, the need for antimicrobial susceptibility testing of *H. pylori* is increasing. Eradication therapy of *H. pylori* usually consists of two different antimicrobial agents and a proton pump inhibitor. Clarithromycin is an important component of the classical triple therapy and in the case of clarithromycin resistant *H. pylori*, the clarithromycin-based regimen results in eradication failure in the vast majority of the cases (Fischbach and Evans, 2007).

Due to the increasing clarithromycin resistance rates (Malfertheiner et al., 2012) the latest European guidelines recommend the use of molecular tests in the detection of *H. pylori* in gastric biopsies and antimicrobial susceptibility testing if culture is not available. Molecular methods have been developed for the detection of *H. pylori* and the simultaneous testing for clarithromycin susceptibility of the isolates. Clarithromycin resistance of *H. pylori* is well known and due to point mutations within the peptidyltransferase region of the 23S rRNA gene.

The high clinical relevance of *H. pylori* infection in gastric mucosa has stimulated the development of several PCR based diagnostic methods detecting *H. pylori* DNA in stool samples. However, the problem of low sensitivity has frequently arisen. These results may have been due to a lack of intact *H. pylori* DNA in stools. In contrast to intestinal bacterial pathogens, which are found in viable form at high concentrations in stools, living *H. pylori* is most likely not present at all and, consequently, its DNA may be present only in a degraded form rendering the detection more challenging. Although some PCR-based methods have shown accurate results in the detection of *H. pylori* and testing of clarithromycin susceptibility in gastric biopsies, problems have arisen when the methods have been used in stool samples. Due to some major limitations, such as PCR inhibitors (Monteneiro, 1997) and low concentrations of mostly fragmented *H. pylori* DNA in fecal samples, it has been difficult to develop methods sensitive enough. The PCR-based methods have only shown sensitivities about 60% when applied for stool samples (Lottspeich, 2007 etc). The purpose of the present study was to develop a highly accurate non-invasive method for detection of *H. pylori* and concomitant clarithromycin susceptibility of the isolate in fecal samples.

Schabereiter-Gurtner et al. (2004) disclosed a real-time PCR assay for detection of *H. pylori* infection and simultaneous clarithromycin susceptibility testing in stool samples. In practice, the authors detected point mutations in the 23S rRNA gene of *H. pylori* associated with clarithromycin resistance. However, Lottspeich et al. (2007) evaluated the method and concluded that detection of *H. pylori* DNA in stool samples by real-time PCR is a difficult task and that this method cannot replace the stool antigen EIA for the accurate diagnosis of *H. pylori* infection. Later, Scaletsky et al. (2011) found that the method proved to be appropriate for *H. pylori* clarithromycin susceptibility testing, although the possibility of missing some positive results should be taken into account. Other publications disclosing primers and/or probes specific to *H. pylori* 23S rRNA gene are: Fontana et al., 2003; Noguchi et al., 2007; Dewhirst et al., 2005; Maeda et al., 1998; Khan et al., 2004; and Rimbara et al., 2005.

PCR assays for detection of *H. pylori* directed to other target genes than the 23S rRNA gene are disclosed in the following publications: Falsafi et al., 2009; Singh et al., 2008; Monteiro et al., 2001; Makristathis et al., 1998; Mishra et al, 2008; and Burucoa et al., 1999.

In the development of PCR assays, one of the most important factors is to locate oligonucleotide sequences that enable reliable species-specific amplification, detection and quantification. It is of utmost importance that a given set of oligonucleotides, designed to amplify *H. pylori*, does not cross-react with DNA originating from any other species possibly present in a sample. Finding such sequences can be far from trivial, at least for the following reasons: 1) Many of the species are relatively closely related, making it challenging to locate sequences that are unique for each species; 2) Pathogen strains originating from a single species can be genetically diverged, making it difficult to locate sequences that would enable equally efficient amplification of all strains within a species; 3) The sample may contain PCR inhibitors or as in this case the sample contains mainly fragmented target DNA, since *H. pylori* typically thrives in gastric mucosa and will very likely die and deteriorate in large intestine. Hence, effective amplification of pathogen DNA from a stool sample requires oligonucleotide design enabling high PCR efficiency (optimally as close to 100% as possible).

Compared to the prior art, the present invention provides at least the following major advantages: the difference of Tm of outer and inner primers is optimized to achieve simpler reaction routines, e.g. the nested PCR reaction of the present invention can be performed in a single vessel. Rimbara et al, 2005, and Noguchi et al., 2007, disclose methods where nested PCR is performed sequentially in two separate reactions. The robustness of the PCR reaction of the present invention is also on the level that there is no need to isolate and purify the DNA from a stool sample by phenol extraction or sample homogenization as is done in Rimbara et al, 2005, and Noguchi et al., 2007, respectively. Furthermore, the length of the amplicon which is amplified in the second reaction of the nested PCR in Rimbara et al, 2005, and Noguchi et al., 2007, is too long to be sensitively detected in real-time PCR. The length of the amplicon amplified by the inner primers of the present invention is 143 bp while in Rimbara it is 463 bp and in Noguchi it is 367 bp.

The disclosures by Fontana et al., 2003, JP 2005168474, and Booka et al., 2005 are not directed to a nested PCR reaction and consequently the primers disclosed are not compatible with nested reactions without modification. Further, the length of the amplicon amplified in Fontana et al., 2003, is 991 bp and is thus too long to be detected in real time PCR. It is also noteworthy that Fontana et al. are amplifying a different region of 23S rRNA gene than Noguchi et al. Therefore, it is clear that the prior art is teaching that there are alternative regions in 23S rRNA which are suitable as target regions for a PCR based detection of the presence of *Helicobacter* strains. In JP 2005168474, the primers seem not to be specific to *Helicobacter* but may also cross-react with *Campylobacter* strains.

Although numerous PCR based assays for detecting *H. pylori* are already disclosed, there is still a need in the field for a PCR assay which is able to provide high specificity and reliability for the detection. The present inventors have now located DNA sequence regions in *H. pylori* 23S rRNA gene that are surprisingly well-suited for specific and sensitive amplification of *H. pylori* DNA from stool. Optimal primers and quantitative PCR probes have been designed and validated for identification of the presence of *H. pylori* in patients.

SUMMARY OF THE INVENTION

The present invention provides a method of detecting *H. pylori* DNA in a stool sample, the method comprising the steps of:

a) performing a PCR reaction comprising DNA isolated from a stool sample as a template and an oligonucleotide primer set specific for amplifying an *H. pylori*-specific target sequence in an *H. pylori* 23S rRNA gene in an amplification reaction, wherein the oligonucleotide primer set comprises an oligonucleotide consisting of at least 10 contiguous nucleotides present in a nucleotide sequence as set forth in SEQ ID NO: 1 and an oligonucleotide consisting of at least 10 contiguous nucleotides present in a nucleotide sequence as set forth in SEQ ID NO: 2; and b) detecting *H. pylori* DNA in said stool sample when the *H. pylori*-specific target sequence is amplified.

The present invention also provides an oligonucleotide primer set comprising an oligonucleotide consisting of at least 10 contiguous nucleotides present in a nucleotide sequence as set forth in SEQ ID NO: 1 and an oligonucleotide consisting of at least 10 contiguous nucleotides present in a nucleotide sequence as set forth in SEQ ID NO: 2, wherein the oligonucleotide primer set amplifies a target sequence in the 23S rRNA gene of *H. pylori*.

The present invention is further directed to a kit for detecting *H. pylori* DNA in a stool sample, the kit comprising the oligonucleotide primer set as described above; and a reagent for performing amplification of a nucleic acid in a PCR reaction.

DETAILED DESCRIPTION OF THE INVENTION

Figure 1:
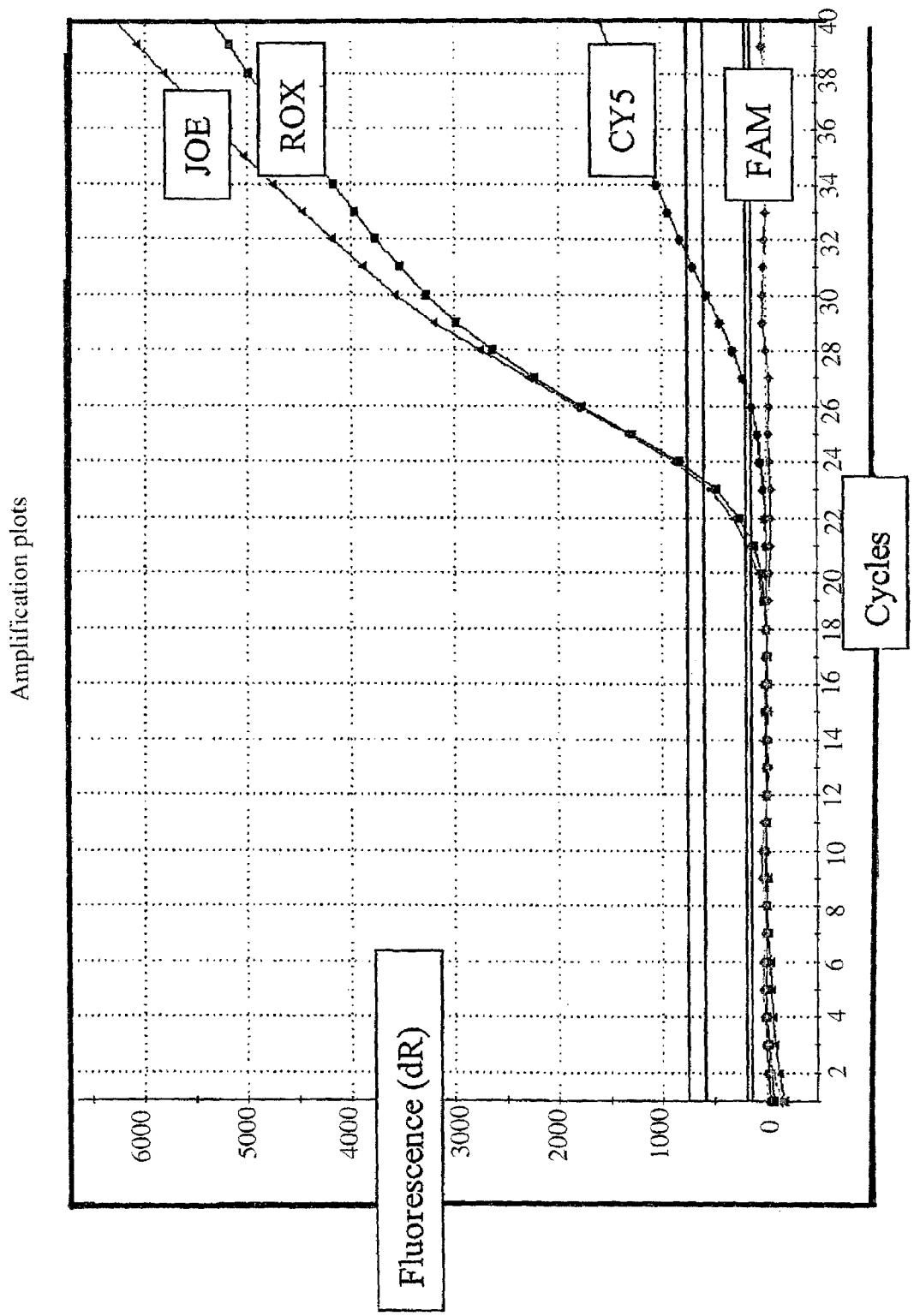
FIG. 1. Positive *H. pylori* result with a conserved region probe (JOE) and positive result for the presence of clarithromycin resistance mutation (ROX). In addition, internal control is positive. Wild type probe (FAM) detecting clarithromycin susceptibility genotype is negative.

As used herein, a "target sequence" present in a nucleic acid sample is a strand of *H. pylori* DNA to be primed and extended by a "primer". A target sequence may be either single-stranded or in a duplex with its complementary sequence. In certain embodiments, a target sequence may not be present in a nucleic acid sample, but may be present later as a result of transcription from another nucleic acid present in said nucleic acid sample. Target sequences may be from any number of sources based on the purpose of the assay being carried out. Target sequence of the present invention is purified to some degree prior to the amplification reactions described herein.

As used herein, the term "oligonucleotide" refers to any polymer of two or more of nucleotides, nucleosides, nucleobases or related compounds used as a reagent in the DNA amplification methods of the present invention. The oligonucleotide may be DNA and/or RNA and/or analogs thereof. The term oligonucleotide does not denote any particular function to the reagent; rather, it is used generically to cover all such reagents described herein. Specific oligonucleotides of the present invention are described in more detail below. As used herein, an oligonucleotide can be virtually any length, limited only by its specific function in the DNA amplification reaction. Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include, but are not limited to base modifications, sugar modifications or backbone modifications. While design and sequence of oligonucleotides for the present invention depend on their function as described below, several variables must generally be taken into account. Among the most critical are: length, G/C content, melting temperature (Tm), Gibb free energy (G), specificity, self-complementarity and complementarity with other oligonucleotides in the system, polypyrimidine (T, C) or polypurine (A, G) stretches, and the 3'-end sequence. Controlling for these and other variables is a standard and well-known aspect of oligonucleotide design, and various computer programs are readily available to screen large numbers of potential oligonucleotides for optimal ones.

As used herein, the term "PCR amplifying" or "PCR amplification" refers generally to cycling polymerase-mediated exponential amplification of nucleic acids employing primers that hybridize to complementary strands, as described for example in Innis et al, PCR Protocols: A Guide to Methods and Applications, Academic Press (1990). Devices have been developed that can perform thermal cycling reactions with compositions containing fluorescent indicators which are able to emit a light beam of a specified wavelength, read the intensity of the fluorescent dye, and display the intensity of fluorescence after each cycle. The amplification product contains a sequence having sequence identity with a target nucleic acid sequence or its complement and can be detected with, for example, an intercalating dye or a detection probe having specificity for a region of the target nucleic acid sequence or its complement. The PCR reaction of the present invention is preferably performed as a real-time PCR assay. As used herein, the term "probe" refers to any of a variety of signaling molecules indicative of amplification. For example, SYBR® Green and other DNA-binding dyes are detector probes. Some detector probes can be sequence-based, for example 5' nuclease probes. Various detector probes are known in the art, for example TaqMan® probes (See U.S. Pat. No. 5,538,848). The melting temperature, Tm, of the probes can be increased by addition of modified nucleotides. The amount of modified nucleotides in one probe is 1, 2, 3, 4 or more. The modified nucleotide can be a LNA nucleotide (Exiqon A/S), minor groove binder (MGB™), SuperBase, or Peptide Nucleic Acid (PNA) or any other modification increasing the Tm of the probe.

*H. pylori* DNA is present only in low level in feces, since *H. pylori* is an upper intestinal track pathogen. Therefore, the right choice of highly specific and sensitive primers is of crucial importance in order to obtain accurate results from a PCR based assay using DNA template isolated from a stool sample. The present invention provides a method and an oligonucleotide primer set for amplifying at least one target sequence of the 23S rRNA gene of *H. pylori*. The developed assay can detect *H. pylori* infection with high sensitivity and simultaneously evaluate clarithromycin resistance. The effect of the invention is particularly related to the choice of target sites for the outer primers, i.e. SEQ ID NOS: 1 and 2.

Accordingly, the present invention is directed to a method of detecting *H. pylori* DNA in a stool sample, the method comprising the steps of:

a) performing a PCR reaction comprising DNA isolated from a stool sample as a template and an oligonucleotide primer set specific for amplifying an *H. pylori*-specific target sequence in an *H. pylori* 23S rRNA gene in an amplification reaction, wherein the oligonucleotide primer set comprises an oligonucleotide consisting of at least 10 contiguous nucleotides present in a nucleotide sequence as set forth in SEQ ID NO: 1 and an oligonucleotide consisting of at least 10 contiguous nucleotides present in a nucleotide sequence as set forth in SEQ ID NO: 2; and b) detecting *H. pylori* DNA in said stool sample when the *H. pylori*-specific target sequence is amplified in step a).

Since nested PCR generally increases sensitivity, said PCR reaction is preferably a nested PCR reaction. Accordingly, a second oligonucleotide primer set can be used in said PCR reaction comprising an oligonucleotide consisting of at least 10 contiguous nucleotides present in a nucleotide sequence as set forth in SEQ ID NO: 3 and an oligonucleotide consisting of at least 10 contiguous nucleotides present in a nucleotide sequence as set forth in SEQ ID NO: 4. Said second oligonucleotide primer set is directed to the amplification of sites of point mutations associated with clarithromycin resistance of certain *H. pylori* strains. The method is thus also further directed to the detection of the mutations in *H. pylori* 23S rRNA gene associated with clarithromycin resistance in *H. pylori*. The presence of said mutations can be detected by a probe or probes detecting the presence of mutations in said gene, preferably at positions corresponding to positions 2514 and/or 2512 of SEQ ID NO:13 (GenBank: U27270.1). Preferably, said mutations are detected by a probe consisting of at least 10 contiguous nucleotides present in a nucleotide sequence as set forth in SEQ ID NO: 7 and/or a probe consisting of at least 10 contiguous nucleotides present in a nucleotide sequence as set forth in SEQ ID NO: 8. Further, for the detection of said mutations a probe or probes consisting of at least 10 contiguous nucleotides present in a nucleotide sequence as set forth in SEQ ID NO: 5 and/or 6 or comprising or consisting of the sequence as set forth in SEQ ID NO: 5 and/or 6 can be used.

One of the most preferred embodiments for the present invention is to perform steps a) and b) of the method in a single vessel (e.g. as described by Strauss et al., 2000). This approach lowers the risk of contamination. To achieve this goal, the melting temperatures of the first and second oligonucleotide primer set must be designed so that the temperature difference between the sets is at least 3 degrees centigrade, preferably 3.5 or 4 degrees centigrade.

The target sequence in *H. pylori* 23S rRNA gene for the first oligonucleotide primer set consisting of SEQ ID NOS: 1 and 2 corresponds to positions 1937-2793 of SEQ ID NO: 13.

The target sequence in *H. pylori* 23S rRNA gene for the second oligonucleotide primer set consisting of SEQ ID NOS: 3 and 4 corresponds to positions 2482-2624 of SEQ ID NO: 13.

Preferably, the detection of *H. pylori* DNA in the stool sample when the *H. pylori*-specific target sequence is amplified is performed using a DNA chip, gel electrophoresis, a radiation measurement, a fluorescence measurement, or a phosphorescence measurement. A person skilled in the art may use the primers and probes of the invention also in other methods and platforms utilizing PCR.

The present invention also provides an oligonucleotide primer set comprising an oligonucleotide consisting of at least 10 contiguous nucleotides present in a nucleotide sequence as set forth in SEQ ID NO: 1 and an oligonucleotide consisting of at least 10 contiguous nucleotides present in a nucleotide sequence as set forth in SEQ ID NO: 2, wherein the oligonucleotide primer set amplifies a target sequence in a 23S rRNA gene of *H. pylori*. Preferably, the oligonucleotide primer set comprises or consists of the nucleotide sequence as set forth in SEQ ID NO: 1 and the nucleotide sequence as set forth in SEQ ID NO: 2.

Preferably, the oligonucleotide primer set further comprises an oligonucleotide consisting of at least 10 contiguous nucleotides present in a nucleotide sequence as set forth in SEQ ID NO: 3 and an oligonucleotide consisting of at least 10 contiguous nucleotides present in a nucleotide sequence as set forth in SEQ ID NO: 4. More preferably, said oligonucleotide primer set comprises or consists of the nucleotide sequence as set forth in SEQ ID NO: 3 and the nucleotide sequence as set forth in SEQ ID NO: 4.

The oligonucleotide primer set may further comprise a probe consisting of at least 10 contiguous nucleotides present in a nucleotide sequence as set forth in SEQ ID NO: 7 and/or a probe consisting of at least 10 contiguous nucleotides present in a nucleotide sequence as set forth in SEQ ID NO: 8. More preferably, said oligonucleotide primer set comprises or consists of the nucleotide sequence as set forth in SEQ ID NO: 7 and the nucleotide sequence as set forth in SEQ ID NO: 8. Most preferably, said oligonucleotide primer set further comprises or consists of the nucleotide sequence as set forth in SEQ ID NO: 5 and the nucleotide sequence as set forth in SEQ ID NO: 6.

The present invention is also providing a kit for detecting *H. pylori* DNA in a stool sample, the kit comprising at least one of the oligonucleotide primer sets as described above; and a reagent for performing amplification of a nucleic acid in a PCR reaction. Preferably, said reagent is selected from a group consisting of DNA polymerase, dNTPs, and a buffer.

The publications and other materials used herein to illuminate the background of the invention, and in particular, to provide additional details with respect to its practice, are incorporated herein by reference. The present invention is further described in the following example, which is not intended to limit the scope of the invention.

EXPERIMENTAL SECTION

The aim in the design phase was to develop a highly *H. pylori* specific PCR that would not amplify other closely related species. The new assay is developed and optimized using sequencing confirmed *H. pylori* strains with and without clarithromycin resistance mutations. Then analytical specificity was tested against 50 clinically relevant pathogenic and non-pathogenic bacterial species, including both gram-negative and gram-positive species. No significant cross-reactivity was detected. The analytical sensitivity with 95% confidence for positive replicas was 10 fg, which corresponds to two genomic copies or one bacterium. The clinical sensitivity and specificity were analysed using gastric biopsy, histology and *Helicobacter* culture with antimicrobial susceptibility testing as a golden standard reference method. Correct identification was achieved in 94% of samples and a correct antimicrobial susceptibility in 90% of a total 80 patient samples studied. As a control, a template from *Oryza sativa*, terminal flower gene Ory, was used.

Nucleid Acid Extraction

The total nucleid acids were extracted using bioMerieux NucliSens Kits, and semi-automated easyMAG instrument for extraction. Both generic and specific B protocol was successfully tested. The specific B protocol was slightly better in qPCR performance, and it was selected for all experiments. A loopful of stool, app. 10% solution, was inoculated into 2 mL of the kit lysis buffer, mixed rigorously for 5 s and incubated at least 15 min in room temperature according to manufacturer's instruction. The extraction volume was 25 µl.

PCR setup and oligonucleotides

The following PCR program and set of oligonucleotides were utilized for all assays performed with Stratagene MxPro 3005P:
1. 95° C. 13 min
2. 94° C. 60
3. 68° C. 90 s
4. 2-3×5 cycles
5. 94° C. 30 s
6. 68° C. 60 s
7. 2-3×15 cycles
8. 94° C. 25 s
9. 64° C. 25 s
10. 8-9×40

Primers

Outer Primers:

```
                                          (SEQ ID NO: 1)
Hpy_sel_003_F   GCTAGTCTAAGGGCGTAGATTGGAGGGAAG (SEQ ID NO: 2)
Hpy_sel_003_R   GCTTGTGCCATTACACTCAACTTGCGATTTC
```

Inner Primers:

```
                                          (SEQ ID NO: 3)
F_Hpyin_06      GGTGAAAATTCCTCCTACC (SEQ ID NO: 4)
R_Hpyin_06      CAAGGATGGCTCCATAAG
```

Control:

```
                                          (SEQ ID NO: 9)
F_ORY_004       CTAATCCCAGCAACCCAACC (SEQ ID NO: 10)
R_ORY_004       CTAATCAATGTGAGACATATGATAGAAATC
```

Probes

```
                                          (SEQ ID NO: 5)
P_Hpy2142wt_02_FAM   CAAGACGGAAAGACCC (SEQ ID NO: 6)
P_Hpyall_02_JOE      CAAAGCCTCCCACCTATCCTGCG (SEQ ID NO: 7)
P_Hpy2143G_06_TEX    CAAGACGGAGAGACCC (SEQ ID NO: 8)
P_Hpy2142GG_05_TEX   CAAGACGGGAAGACCC (SEQ ID NO: 11)
P_Ory_4_Cy5          CCTGCACTGGTAAGCTATG
```

The underlined nucleotides in the above list are LNA nucleotides (Exiqon A/S) increasing the Tm of the probe.

Synthetic Ory Template

```
                                          (SEQ ID NO: 12)
TGCTCCTAATCCCAGCAACCCAACCTTGAGGGAATACCTGCACTGGTAA

GCTATGCTCTTGCAATTGTTGTGATTTCTATCATATGTCTCACATTGAT

TAGTGATCTA
```

| Reaction mix | | |
|---|---|---|
| dH2O | | 2.85 µl |
| Qiagen NoRox mastermix | | 12.5 µl |
| Hpy_sel_003_F | 0.125 µM | 0.15 µl |
| Hpy_sel_003_R | 0.125 µM | 0.15 µl |
| F_Hpyin_06 | 0.8 µM | 1 µl |
| R_Hpyin_06 | 0.8 µM | 1 µl |
| F_ORY_004 | 0.125 µM | 0.15 µl |
| R_ORY_004 | 0.125 µM | 0.15 µl |
| P_Hpy2142wt_02_FAM | 0.2 µM | 0.25 µl |
| P_Hpyall_02_JOE | 0.28 µM | 0.35 µl |
| P_Hpy2143G_06_TEX | 0.28 µM | 0.35 µl |
| P_Hpy2142GG_05_TEX | 0.28 µM | 0.35 µl |
| P_Ory_4_Cy5 | 0.2 µM | 0.25 µl |
| Synthetic Ory template | 10exp-11 | 0.5 µl |
| Template | | 5 µl |
| Total premix | | 25 µl |

After initial denaturation and polymerase activation 5 cycles of long extension time was utilized to improve amplification efficacy from less optimal genomic DNA. After generating the few initial copies, the long specific amplification phase was continued 15 more cycles, but no more to maximize amplification efficacy in the following steps (i.e. 8.-10.). Surprisingly, a longer first phase than 20 (5+15) cycles decreased sensitivity and caused a risk for too early amplification in the clarithromycin resistance mutation detection phase leading to great problems with data analysis. The annealing temperature was carefully optimized similar for all probes to be able to detect of single nucleotide mutation. It was difficult to design high sensitivity probes due to rather low melting temperature requirement, which was necessary to avoid putative unintended probe binding in the earlier high temperature specific amplification phase.

Example 1

Positive *H. pylori* result with a conserved region probe (JOE) and positive result for the presence of clarithromycin resistance mutation (ROX). In addition, internal control is positive. Wild type probe (FAM) detecting clarithromycin susceptibility is negative. See FIG. 1 for results.

FAM (green): wild type genotype within clarithromycin mutation hot spot. When positive, no resistance mutation present. Treatment with clarithromycin based combination likely successful.

JOE (yellow): highly conserved region in the lagging strand, indicates presence of *H. pylori* in the sample regardless resistance mutations present.

Note! If a new, or a double mutation appears, the JOE is the only positive probe in addition to internal control=clarithromycin resistant genotype present.

ROX (red): a mutation in A2142G or A2143G position linked to clarithromycin resistance. The most common types detected.

CY5 (far red): inhibition control.

Example 2

Figure 2:
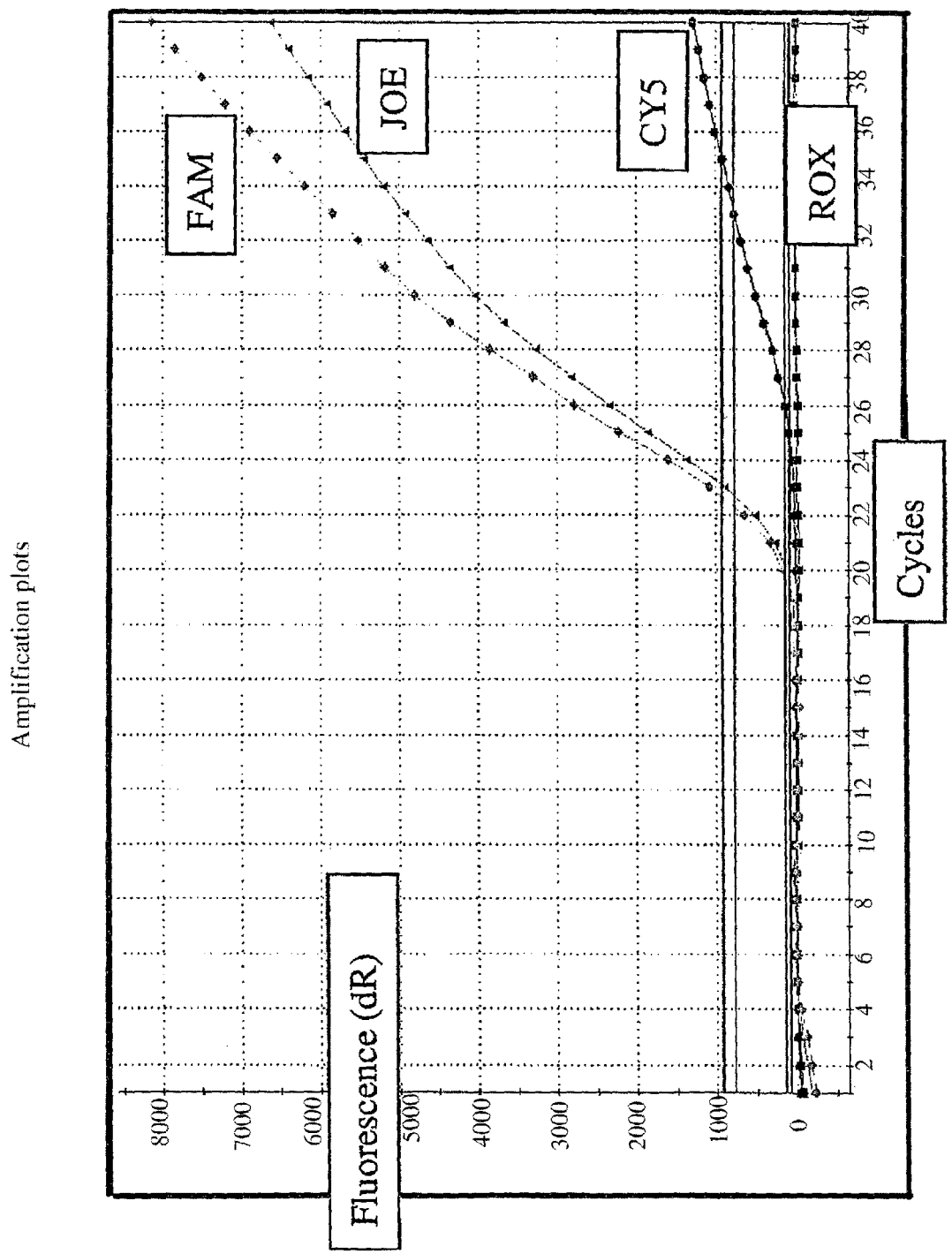
FIG. 2. Positive *H. pylori* result with a conserved region probe (JOE) and positive result for the presence of wild type probe (FAM) excluding clarithromycin resistance mutation. In addition, internal control (CY5) is positive. Resistance mutation probes detecting clarithromycin resistance (ROX) are negative. See FIG. 2 for results.

Positive *H. pylori* result with a conserved region probe (JOE) and positive result for the presence of wild type probe (FAM) excluding clarithromycin resistance mutation. In addition, internal control (CY5) is positive. Resistance mutation probes detecting clarithromycin resistance (ROX) are negative. See FIG. 2 for results.

Example 3

Figure 3:
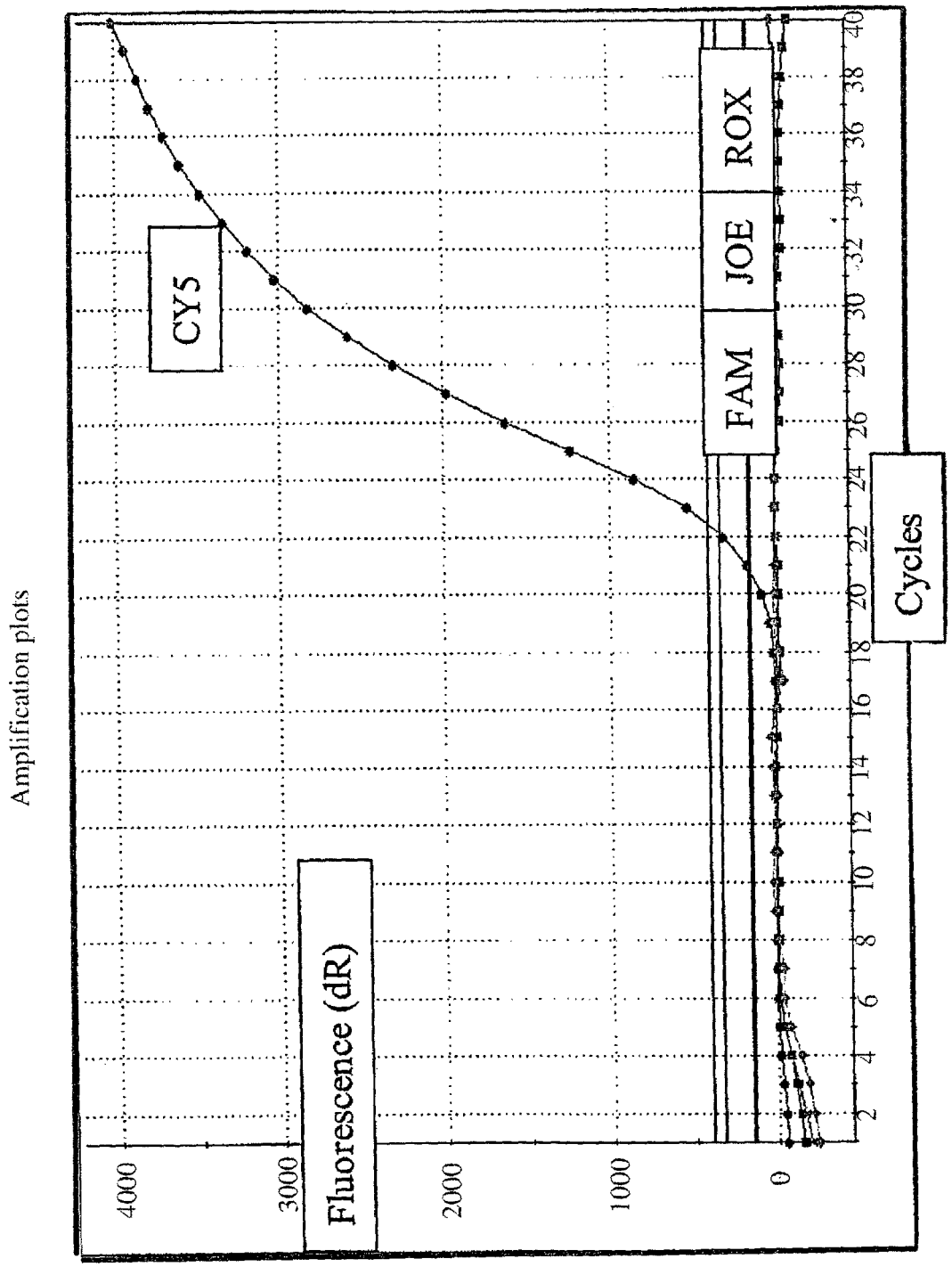
FIG. 3. Negative result for *H. pylori*: only internal control is positive, no PCR inhibition detected. See FIG. 3 for results.

Negative result for *H. pylori*: only internal control is positive, no PCR inhibition detected. See FIG. 3 for results.

REFERENCES

Booka et al., 2005, *Helicobacter*, 10:205-213
Burucoa et al., 1999, Journal Of Clinical Microbiology, 37(12):4071-4080
Chey and Wong, 2007, Am J Gastroenterol, 102:1808-1825
Dewhirst et al., 2005, Journal Of Bacteriology, 187(17): 6106-6118
Falsafi et al., 2009, World J Gastroenterol, 15(4): 484-488
Fischbach and Evans, 2007, Aliment Pharmacol Ther 2007; 26:343e57
Fontana et al., 2003, Journal Of Clinical Microbiology, 41(8):3636-3640
Ford et al., 2003, The Cochrane Database of Systematic Reviews 2003, Issue 4.
Ford et al., 2004, Am J Gastroenterol, 99:1833-1855
Khan et al., 2004, Antimicrobial Agents And Chemotherapy, 48(9):3567-3569
Kosunen et al., 2011, Int. J. Cancer: 128:433-439
Lottspeich, 2007, Journal Of Clinical Microbiology, 45(6):1718-1722
Maeda et al., 1998, Gut, 43:317-321
Makristathis et al., 1998, Journal Of Clinical Microbiology, 36(9):2772-2774
Malfertheiner et al., 2012, Gut 61:646e664
Mishra et al, 2008, J Infect Developing Countries. 2(3): 206-210
Monteiro et al., 2001, Journal of Microbiological Methods. 45:89-94
Noguchi et al., 2007, Journal of Medical Microbiology, 56, 1174-1180
Rimbara et al., 2005, Current Microbiology, 51:1-5
Scaletsky et al., 2011, *Helicobacter*, 16: 311-315
Schabereiter-Gurtner et al., 2004, Journal Of Clinical Microbiology, 42(10):4512-4518
Singh et al., 2008, *Helicobacter*, 13(1): 30-34
Strauss et al., 2000, Diagnostic Molecular Pathology 9(3): 151-157, 2000

The invention claimed is:

1. A method of detecting *Helicobacter pylori* DNA in a stool sample, the method comprising:
   a) performing a nested PCR reaction comprising DNA isolated from a stool sample as a template and a first and second oligonucleotide primer set specific for amplifying *H. Pylori*-specific target sequences in an *H. pylori* 23S rRNA gene in an amplification reaction,
   wherein the first oligonucleotide primer set comprises an oligonucleotide primer comprising the nucleotide sequence as set forth in SEQ ID NO: 1 or consisting of at least 10 contiguous nucleotides present in the nucleotide sequence as set forth in SEQ ID NO: 1 and an oligonucleotide primer comprising the nucleotide sequence as set forth in SEQ ID NO: 2 or consisting of at least 10 contiguous nucleotides present in the nucleotide sequence as set forth in SEQ ID NO: 2,
   wherein the second oligonucleotide primer set comprises an oligonucleotide primer comprising the nucleotide sequence as set forth in SEQ ID NO: 3 or consisting of at least 10 contiguous nucleotides present in the nucleotide sequence as set forth in SEQ ID NO: 3 and an oligonucleotide primer comprising the nucleotide sequence as set forth in SEQ ID NO: 4 or consisting of at least 10 contiguous nucleotides present in the nucleotide sequence as set forth in SEQ ID NO: 4,
   wherein the *H. pylori*-specific target sequence of the first oligonucleotide primer set is a nucleotide region of an *H. pylori* 23S rRNA gene corresponding to positions 1937-2793 of SEQ ID NO: 13 and at least part of said nucleotide region is amplified in the PCR reaction by the first oligonucleotide primer set, and
   wherein the *H. Pylori*-specific target sequence of the second oligonucleotide primer set is a nucleotide region of an *H. pylori* 23S rRNA gene corresponding to positions 2482-2624 of SEQ ID NO: 13 and at least part of said nucleotide region is amplified in the PCR reaction by the second oligonucleotide primer set; and
   b) detecting *H. pylori* DNA in said stool sample when the *H. pylori*-specific target sequences are amplified.

2. The method according to claim 1, wherein the mutations in *H. pylori* 23S rRNA gene associated with clarithromycin resistance in *H. pylori* are further detected by a first probe consisting of at least 10 contiguous nucleotides present in a nucleotide sequence as set forth in SEQ ID NO: 7 and a second probe consisting of at least 10 contiguous nucleotides present in a nucleotide sequence as set forth in SEQ ID NO: 8 or wherein said first probe comprises the nucleotide sequence as set forth in SEQ ID NO: 7 and said second probe comprises the nucleotide sequence as set forth in SEQ ID NO: 8.

3. The method according to claim 1 or 2, wherein the detection of *H. pylori* DNA in the stool sample when the *H. pylori*-specific target sequences are amplified is performed using a DNA chip, gel electrophoresis, a radiation measurement, a fluorescence measurement, or a phosphorescence measurement.

4. The method according to claim 1, wherein steps a) and b) are performed in a single vessel.

5. The method according to claim 1, wherein said method is performed as a real-time PCR assay.

* * * * *

SEQUENCE LISTING

<160> NUMBER OF SEQ ID NOS: 13

<210> SEQ ID NO 1
<211> LENGTH: 30
<212> TYPE: DNA
<213> ORGANISM: Helicobacter pylori

<400> SEQUENCE: 1

```
gctagtctaa gggcgtagat tggagggaag                                    30

<210> SEQ ID NO 2
<211> LENGTH: 31
<212> TYPE: DNA
<213> ORGANISM: Helicobacter pylori

<400> SEQUENCE: 2
gcttgtgcca ttacactcaa cttgcgattt c                                  31

<210> SEQ ID NO 3
<211> LENGTH: 19
<212> TYPE: DNA
<213> ORGANISM: Helicobacter pylori

<400> SEQUENCE: 3
ggtgaaaatt cctcctacc                                                19

<210> SEQ ID NO 4
<211> LENGTH: 18
<212> TYPE: DNA
<213> ORGANISM: Helicobacter pylori

<400> SEQUENCE: 4
caaggatggc tccataag                                                 18

<210> SEQ ID NO 5
<211> LENGTH: 16
<212> TYPE: DNA
<213> ORGANISM: Helicobacter pylori

<400> SEQUENCE: 5
caagacggaa agaccc                                                   16

<210> SEQ ID NO 6
<211> LENGTH: 23
<212> TYPE: DNA
<213> ORGANISM: Helicobacter pylori

<400> SEQUENCE: 6
caaagcctcc cacctatcct gcg                                           23

<210> SEQ ID NO 7
<211> LENGTH: 16
<212> TYPE: DNA
<213> ORGANISM: Helicobacter pylori

<400> SEQUENCE: 7
caagacggag agaccc                                                   16

<210> SEQ ID NO 8
<211> LENGTH: 16
<212> TYPE: DNA
<213> ORGANISM: Helicobacter pylori

<400> SEQUENCE: 8
caagacggga agaccc                                                   16

<210> SEQ ID NO 9
<211> LENGTH: 20
<212> TYPE: DNA
<213> ORGANISM: Oryza sativa

<400> SEQUENCE: 9
```

```
ctaatcccag caacccaacc                                              20

<210> SEQ ID NO 10
<211> LENGTH: 30
<212> TYPE: DNA
<213> ORGANISM: Oryza sativa

<400> SEQUENCE: 10
ctaatcaatg tgagacatat gatagaaatc                                   30

<210> SEQ ID NO 11
<211> LENGTH: 19
<212> TYPE: DNA
<213> ORGANISM: Oryza sativa

<400> SEQUENCE: 11
cctgcactgg taagctatg                                               19

<210> SEQ ID NO 12
<211> LENGTH: 108
<212> TYPE: DNA
<213> ORGANISM: Oryza sativa

<400> SEQUENCE: 12
tgctcctaat cccagcaacc caaccttgag ggaatacctg cactggtaag ctatgctctt   60
gcaattgttg tgatttctat catatgtctc acattgatta gtgatcta              108

<210> SEQ ID NO 13
<211> LENGTH: 3857
<212> TYPE: DNA
<213> ORGANISM: Helicobacter pylori

<400> SEQUENCE: 13
aaagcttcat ccacccccc  catcccatca tttccaatca ctttatcca  tttctttcaa   60 acccaaaaac tttaagcaaa cttttaagcat gtctataatt acatttcgtt ttaaagacaa  120
gcttaaaaag tctttaattg aaccactcaa acaagttcta caagctaaag ctttaaataa  180
aacccaccag ctggtaaaac ttgagtgtta taaaaagatt agggatcaag cattttttagt 240 cttcttttaag ggtttaacat taagagtgat tatagcaagt ttttaaagaa aaacgaagtt  300
atttgattta acattgttaa tagcctatgt aaaagtaaag taaaactaca ataactctgt   360
cttatattca ttaaggcagt ggtagcgctg aagaatgttc gtgcaattgt cgttattcat   420
tataaaaggg cgggttttaa aggatatttt aaaatttaaa acaagctttt aagagcagat   480
ggcggatgcc ttgccaaaga gaggcgatga aggacgtact agactgcgat aagctatgcg   540
gagctgtcaa ggagctttga tgcgtagatg tccgaatggg gcaacccaac taatagagat   600
attagttact ctaacagaga gcgaacctag tgaagtgaaa catctcagta actagaggaa   660
aagaaatcaa cgagattccc taagtagtgg cgagcgaacg gggaaaaggg caaaccgagt   720
gcttgcattc gggggttgagg actgcaacat ccaagagaac gctttagcag agttacctgg   780
aaaggtaagc catagaaagt gatagccttg tatgcgacaa ggcgttttta ggtagcagta   840
tccagagtag gccaggacac gaggaatcca ggttgaagcc gggagacca  ctctccaact   900 ctaaatacta ctctttgagc gatagcgaac aagtaccgtg agggaaaggt gaaaagaacc   960
gcagtgagcg gagtgaaata gaacctgaaa ccatctgctt acaatcattc agagccctat  1020
gatttatcag ggtgatggac tgccttttgc ataatgatcc tgcgagttgt ggtatctggc  1080
```

```
aaggttaagc gaatgcgaag ccgtagcgaa acgagttctt aatagggcga acaagtcaga    1140
tgctgcagac ccgaagctaa gtgatctatc catggccaag ttgaaacgcg tgtaatagcg    1200
cgtggaggac tgaactccta cccattgaaa cgggttggga tgagctgtgg ataggggtga    1260
aaggccaaac aaacttagtg atagctggtt ctcttcgaaa tatatttagg tatagcctca    1320
agtgataata aaggggggta gagcgctgat tgggctaggg ctgctcgccg cggtaccaaa    1380
ccctatcaaa cttcgaatac cttttatcgt atcttgggag tcaggcggtg ggtgataaaa    1440
tcaatcgtca aaggggaac aacccagact accaaataag gtccctaagt tctattctga    1500
gtggaaaaag atgtgtggct actaaaacaa ccaggaggtt ggcttagaag cagccatcct    1560
ttaaagaaag cgtaacagct cactggtcta gtggtcatgc gctgaaaata taacgggct     1620 aagatagaca ccgaatttgt agattgtgtt aaacacagtg gtagaagagc gttcatacca    1680
gcgttgaagg tataccggta aggagtgctg gagcggtatg aagtgagcat gcaggaatga    1740
gtaacgataa gatatatgag aattgtatcc gccgtaaatc taaggtttcc tacgcgatgg    1800
tcgtcatcgt agggttagtc gggtcctaag ccgagtccga aaggggtagg tgatggcaaa    1860
ttggttaata ttccaatacc gactgtggag cgtgatgggg ggacgcatag ggttaagcga    1920
gctagctgat ggaagcgcta gtctaagggc gtagattgga gggaaggcaa atccacctct    1980
gtatttgaaa cccaaacagg ctcttttgagt ccttttagga caagggaga atcgctgata    2040 ccgtcgtgcc aagaaaagcc tctaagcata tccatagtcg tccgtaccgc aaaccgacac    2100
aggtagatga gatgagtatt ctaaggcgcg tgaaagaact ctggttaagg aactctgcaa    2160
actagcaccg taagttcgcg ataaggtgtg ccacagcgat gtggtctcag caaagagtcc    2220
ctcccgactg tttaccaaaa acacagcact tgccaactc gtaagaggaa gtataaggtg    2280
tgacgcctgc ccggtgctcg aaggttaaga ggatgcgtca gtcgcaagat gaagcgttga    2340
attgaagccc gagtaaacgg cggccgtaac tataacggtc ctaaggtagc gaaattcctt    2400
gtcggttaaa taccgacctg catgaatggc gtaacgagat gggagctgtc tcaaccagag    2460
attcagtgaa attgtagtgg aggtgaaaat tcctcctacc cgcggcaaga cggaaagacc    2520
ccgtggacct ttactacaac ttagcactgc taatgggaat atcatgcgca ggataggtgg    2580
gaggctttga agtaagggct ttggctctta tggagtcatc cttgagatac caccccttgat    2640 gtttctgtta gctaactggc ctgtgttatc cacaggcagg acaatgcttg gtgggtagtt    2700
tgactggggc ggtcgctcct aaaaagtaac ggaggcttgc aaaggttggc tcattgcggt    2760
tggaaatcgc aagttgagtg taatggcaca agccagcctg actgtaagac atacaagtca    2820
agcagagacg aaagtcggtc atagtgatcc ggtggttctg tgtggaaggg ccatcgctca    2880
aaggataaaa ggtaccccgg ggataacagg ctgatctccc ccaagagctc acatcgacgg    2940
ggaggtttgg cacctcgatg tcggctcatc gcatcctggg gctggagcag gtcccaaggg    3000
tatggctgtt cgccatttaa agcggtacgc gagctgggtt cagaacgtcg tgagacagtt    3060
cggtccctat ctgccgtggg cgtaggaaag ttgaggagag ctgtccctag tacgagagga    3120
ccgggatgga cgtgtcactg gtgcaccagt tgtctgccaa gagcatcgct gggtagcaca    3180
cacggatgtg ataactgctg aaagcatcta agcaggaacc aactccaaga taaactttcc    3240
ctgaagctcg cacaaagact atgtgcttga tagggtagat gtgtgagcgc agtaatgcgt    3300
ttagctgact actactaata gagcgtttgg cttgtttttt gcttttgat aagataacgg     3360 caataagcgc gaatgggtta ccactgccct actgagtgta agagagttgg agttttatga    3420
agacttttat aagattaaac tttaatgagg aatgagatac catctcaatg gtttaaagtt    3480
```

```
aaaggctatt aacgatcttc tttgttaaaa acagctcccc tataaagaga aagggagtt      3540 aagggtaaat gcgtttttat ctttagctcc cttttccttg tgcctttaga gaagaggaac     3600
tacccagtta accattccga acctggaagt caagctcttc atcgctgata atactgctct     3660
tttcaagagt gggaatgtag gtcggtgcag ggatagggaa atgttttttt agtcttgctt     3720
ttttatttga tttcattatt gactcattgt tttgtttgtt taggtggttt attggggttt     3780
ggttgttttg ttgatttagt tttcatgctc taaaccgatg aaaggttgtt tgaagtcttc     3840
tctgttcata aacttgc                                                    3857
```